United States Patent [19]

Freeman

[11] Patent Number: 4,670,015
[45] Date of Patent: Jun. 2, 1987

[54] HIP IMPLANT

[75] Inventor: Michael A. R. Freeman, London, England

[73] Assignee: Finsbury (Instruments) Limited, London, England

[21] Appl. No.: 720,901

[22] Filed: Apr. 8, 1985

[30] Foreign Application Priority Data

Apr. 13, 1984 [GB] United Kingdom ............... 8409714

[51] Int. Cl.$^4$ ............................................. A61F 2/32
[52] U.S. Cl. ....................................................... 623/23
[58] Field of Search ............................. 623/21, 22, 23; 128/92 C, 92 CA

[56] References Cited

U.S. PATENT DOCUMENTS 4,080,666  3/1978  Fixel ............................. 128/92 CA

FOREIGN PATENT DOCUMENTS 0073057  3/1983  European Pat. Off. .............. 623/23
 560042  3/1975  Switzerland ......................... 623/23
1371335 10/1974  United Kingdom ................. 623/23
1489887 10/1977  United Kingdom.
2104391  3/1983  United Kingdom ................. 623/22
2118043 10/1983  United Kingdom ................. 623/23

OTHER PUBLICATIONS

Journal of Bone & Joint Surgery, vol. 44—A, No. 6, Adv. p. 73, Sep. 1962.

Primary Examiner—Richard J. Apley
Assistant Examiner—David J. Isabella
Attorney, Agent, or Firm—Lee, Smith & Zickert

[57] ABSTRACT

A hip implant has a stem portion with a substantially linear axis and a circular cross-section at least in the region of the bottom end thereof. A wedge-shaped portion extends medially from the stem at or near the top end of the stem. The wedge-shaped portion is surmounted by a ball.

8 Claims, 7 Drawing Figures

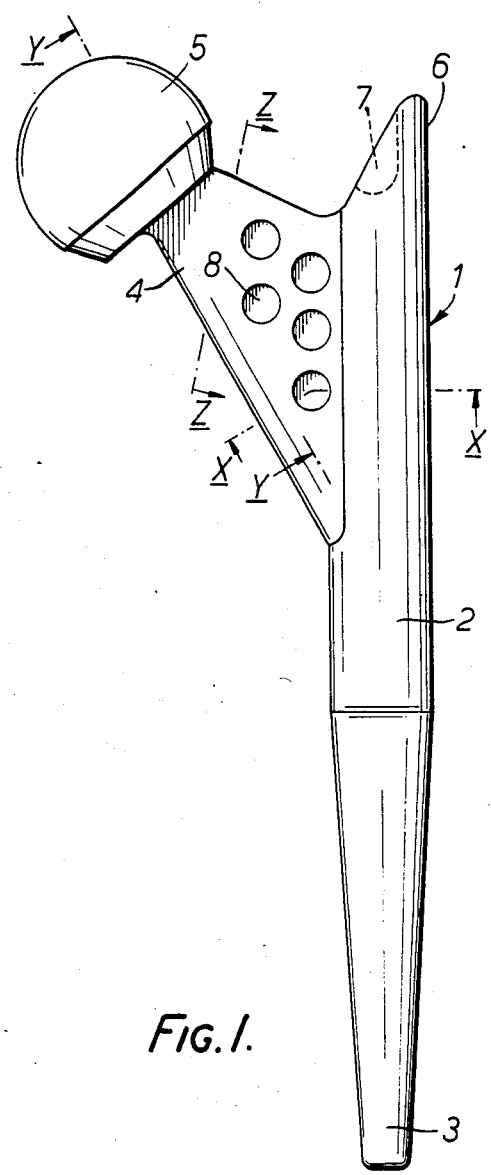
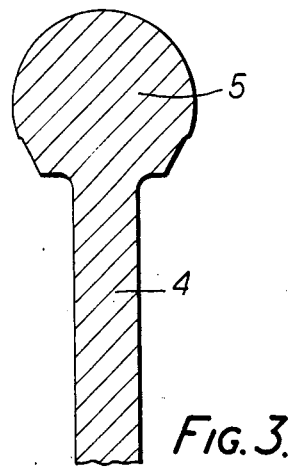
Fig. 3.
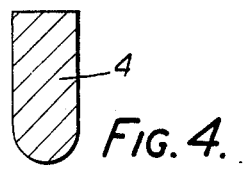
Fig. 4.
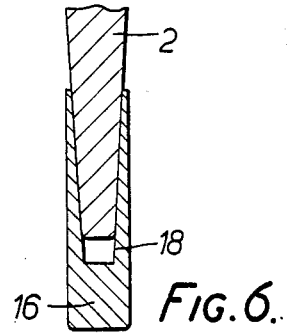
Fig. 6.
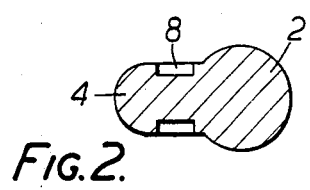
Fig. 1.
Fig. 2.
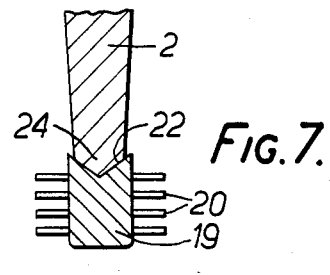
Fig. 7.

HIP IMPLANT

FIELD OF THE INVENTION

This invention relates to artificial bone implants and is particularly concerned with implants for replacing hip joints.

BACKGROUND OF THE INVENTION

The efficient functioning of the hip joints is extremely important to the well being and mobility of the human body. Each hip joint is constituted by the upper portion of the upper leg bone (femur) which terminates in an offset bony neck surmounted by a ball-headed portion which rotates within a socket (acetabulum) in the hip bone. Diseases such as rheumatoid- and osteo-arthritis can cause erosion of the cartilage lining the acetabulum so that the ball of the femur and hip bone rub together causing pain and further erosion. Bone erosion causes the bones themselves to attempt to compensate and reshape, thus giving a misshapen joint which may well cease to function altogether.

DESCRIPTION OF THE PRIOR ART

The replacement of the hip joint by an artificial implant is widely practised but the implants conventionally used can suffer from a number of disadvantages.

Thus, conventional hip implants are usually inserted by resecting the neck of the femur and reaming a comparatively large cavity down the femur to receive a bow-shaped implant surmounted by a ball which is then cemented in place using, for example, an acrylic filler material. The implant is bow-shaped to correspond to the angle which the intact femur ball head makes with the downwardly extending stem of the femur. Examples of such hip implants are shown in GB Patent Specification Nos. 1409053 and 1409054.

The bottom portion of the implant, while tapering, is conventionally of non-circular flattened cross-section so as to resist rotational forces within the reamed cavity. Such an implant, if correctly cemented can be comparatively efficient but, if not correctly cemented, or after a long period of use, the cement may work loose, thus allowing movement of the implant and causing bone erosion. Bone erosion can lead to tissue reactions which themselves can lead to further bone destruction. As a result, the whole joint can get out of alignment and/or damaged beyond repair.

Furthermore the practice of removing almost completely the bony neck of the femur is destructive of bone and against the accepted advantages of conserving as much bone as possible. A further result of the shape of conventional implants and the removal of much of the bony neck (which in a healthy hip bone provides reinforcement) is the problem of so-called "stress shielding". Thus, with a conventional implant, both compression and torsional loads are being borne by the lower portion of the implant projecting down the stem of the femur and not by the upper bowed portion adjacent the ball. This can lead to fatigue failure of the implant itself and/or undue loading of the adjacent portions of the femur. Because the remaining uppermost portions of the femur are shielded from load they themselves may start to disappear.

A further problem with conventional implants is that it is difficult to correctly ream a cavity in the correct bowed configuration. This can lead to errors in positioning the ball head with respect to the acetabulum or femur, thus preventing the normal range of hip movement and/or causing unwanted bone impaction and may even lead to the shortening of one leg with a resultant limp. Finally, the curved shape of the implant and the presence of cement make removal for replacement purposes extremely difficult.

OBJECTS OF THE INVENTION

It is an object of the present invention to provide a hip implant which removes or at least minimizes the problems outlined above.

It is a further object of the invention to provide a hip implant which does not necessarily require the use of cement and which can be readily removed and/or replaced.

It is a further object of the invention to provide a hip implant which minimizes the destruction of bone and deviates the problem of stress shielding.

SUMMARY OF THE INVENTION

According to this invention, we provide a hip implant comprising a stem portion, with a substantially linear axis, having, at least in the region of one end thereof, a substantially circular cross-section and a wedge-shaped portion extending medially from the stem portion at or near the opposite end to the said one end, the wedge-shaped portion being surmounted by a ball.

According to a further aspect of the invention, we provide a method of introducing to a human body a hip implant comprising:

a stem portion, having a substantially linear axis, and at least in the region of one end thereof, a substantially circular cross-section;

a wedge-shaped portion, extending medially from the stem portion at or near the opposite end to the said one end, and a ball surmounting the wedge-shaped portion, which method comprises:

removing the ball from the bony neck of the human femur;

reaming an aperture in the femur of a size to snugly receive the stem of the implant;

providing a slot in the bony neck of said femur of a size to receive the wedge-shaped portion; and positioning said implant in the aperture and slot with the ball projecting beyond the bony neck of the femur.

DESCRIPTION OF THE PREFERRED EMBODIMENTS

Preferably the end of the stem opposite the said one end extends past the junction with the wedge-shaped portion to a point level with the ball and said opposite end may have means such as a drilled hole for receiving a hook or the like, for use in any necessary removal of the implant. Preferably the wedge-shaped portion is of flattened section so that, in use, it does not displace any greater portion of bony neck than is necessary. The wedge-shaped portion may be textured and/or have indentations to encourage bone interlock, e.g. by grafting to the adjacent bone. Preferably the stem is tapered at said one end.

One form of the invention will now be described with reference to the accompanying drawings, wherein FIG. 1 is a side view of an implant according to the invention;

FIG. 2 is a section on line X—X of FIG. 1;

FIG. 3 is a partial section on line Y—Y of FIG. 1;

FIG. 4 is a section on line Z—Z of FIG. 1;

FIG. 6 is a partial cross sectional view of an implant having an end stop; and

FIG. 7 is a view similar to that of FIG. 6 having a different form of end stop.

Figure 5:
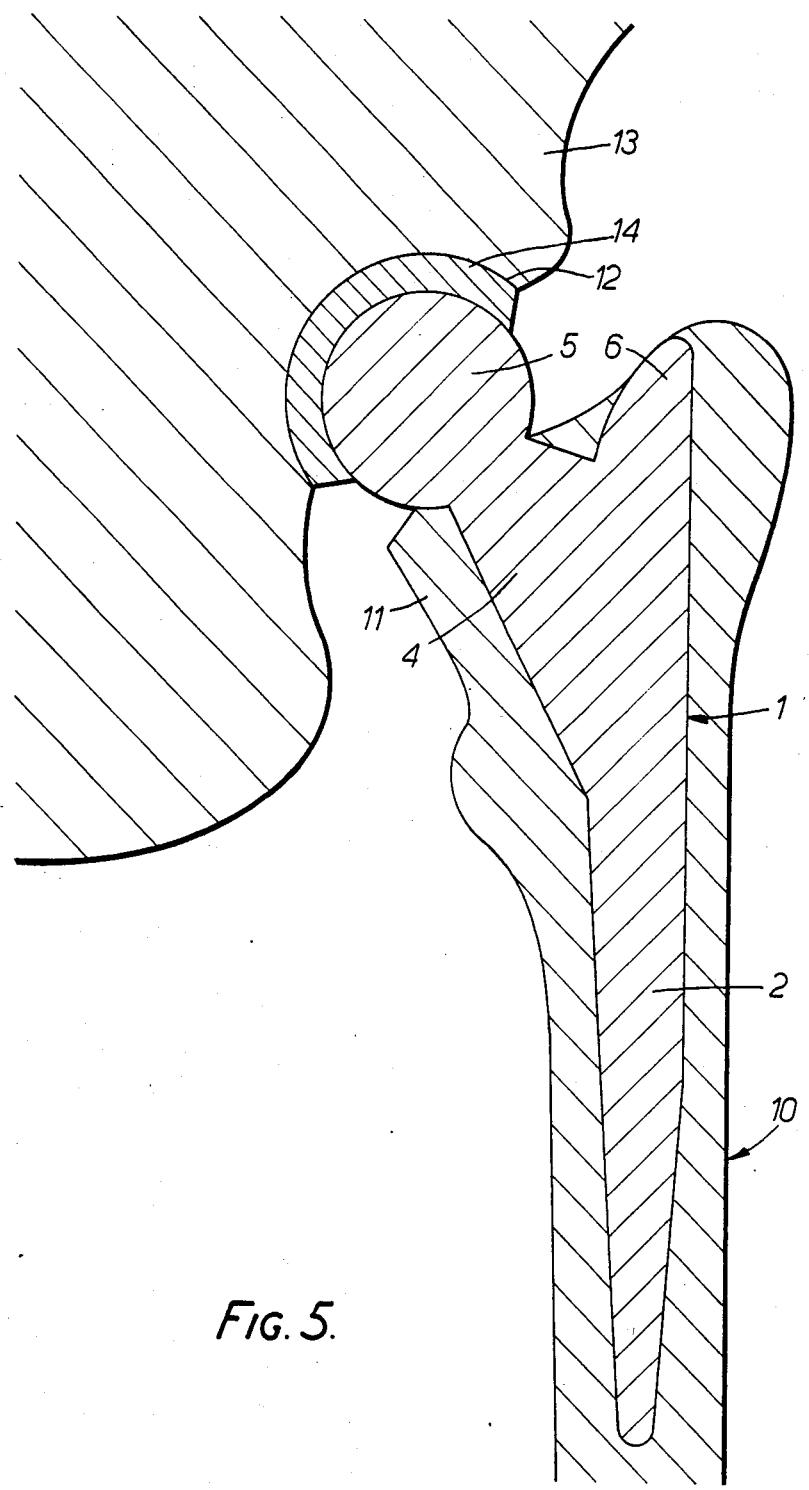
FIG. 5 is a side view of a hip joint incorporating the implant of FIG. 1.

The implant 1 shown in the drawings is of an acceptable material for introduction to the human body such as a cobalt-chromium alloy or titanium alloy. It may be all of one material or may have a ball head portion of a different material such as a ceramic. The implant 1 comprises a stem 2 which has a substantially linear axis and a substantially circular cross-section as can be seen from FIG. 2. The stem 2 tapers towards its lower end 3, the extent of the taper or even absence of any taper depending on individual needs. Spaced from the tapered portion 3, a flattened wedge portion 4 extends medially (i.e. in use, towards the middle of the body) from the stem 2 and is surmounted by a ball head 5. The stem 2 extends beyond the wedge portion 4 to form a projecting end 6 for lateral support and provided with an aperture 7, which, in use, can receive a hook or like means for removing the implant from the bone if this becomes necessary. Wedge portion 4 is provided with indentations 8 which, when the implant is in place, can assist in encouraging bone interlock, e.g. by grafting of the adjacent bone to the implant 1. Wedge portion 4 may also be gradually reduced in thickness from the proximal to the distal end to assist interference interlock with the bone, especially when the wedge portion has a textured surface.

The provision of a separable ball head may be used to adjust neck length for individual needs. Thus ball heads incorporating varying neck lengths can be fitted to standard stems with shortened wedge portions.

The surface of the implant 1 can be modified as desired. Thus it may, for example, be plain, textured or coarse blasted, or coated with an inert metal or other material or certain areas of the implant may be coated with material to give a porous surface.

FIG. 5 illustrates the position occupied by the implant when in use in a human body. Thus the femur 10 of a human body has had the ball removed from the top of the bony neck 11. It is to be particularly noted that most of the bony neck remains intact throughout its length except for a slot entering its superior surface and that the distal part of the femoral head is also retained. An implant 1 according to the invention has been introduced to the femur 10 by accurately reaming an aperture down the femur 10 to snugly receive the stem 2 of implant 1 while the bony neck 11 of the femur 10 is provided with an accurately machined slot and bone removed only to the extent necessary to receive the comparatively thin wedge portion 4 of the implant 1. The ball head 5 of the implant 1 projects from the neck 11 within the acetabulum 12 formed in the hip bone 13. The acetabulum may contain a synthetic lining insert 14 of suitable physiologically acceptable synthetic material to replace the worn cartilage of the joint and provide a bearing surface for the ball head 5. Care must be taken in the choice of the size and shape of the lining insert 14 so that there is no danger of bone impaction against the neck 11 and consequent damage during motion of the joint. There is a comparatively small area at the base of the ball head 5 resting on the neck.

It will be seen that several advantages follow from the construction described above.

The provision of a stem with a substantially linear axis and circular cross-section means that an accurate cavity can be reamed in the femur by precision instruments, thus minimising the loss of bone and allowing the implant to be precision fit without the need for cement. Of course, an even layer of some cement can be used if desired but should generally be unnecessary at least for a primary implant. The accuracy of implantation also ensures that the femur with its implant is correctly orientated both laterally and vertically with respect to the hip bone.

The cavity in the femur 10 may have a separate end stop fitted in the base of the cavity. Examples of such end stops are shown in FIGS. 6 and 7. In FIG. 6, a generally cylindrical end stop 16 has a tapered channel 18 to receive the correspondingly tapered end of stem 2. In FIG. 7, an end stop 19 has fins 20 extending sideways therefrom to facilitate grapling with the adjacent portion of the femur. Stop 19 has an indentation 22 at the top thereof contoured to receive the pointed end 24 of the stem 2 of the implant. The end stops 16 and 19 can serve several useful purposes such as centralisation of the stem tip within the femur cavity, and ability to act as cavity occluders and to provide progressive stress transfer at the stem tip.

The provision of wedge portion 4 within the bony neck 11 anchors the implant against torsional forces and means that the stem 2 can be of circular cross-section, the overall shape greatly facilitating its removal if necessary. Further there has been no need to resect the bony neck 11, with consequent saving of bone, thus enabling the neck 11 to carry a great deal of the compression and torsional load on the joint via the wedge portions. This obviates the problem of "stress shielding" discussed above and greatly helps to stabilize the prosthesis within the femur. Thus the main load is carried down within the wedge and to the top portion of the bone.

If it is desired to remove the implant, it is a simple matter to cut any grafting which may have occurred in the region of wedge portion 4 and neck 11 as this is of easy access. The absence of cement and the straight nature of stem 2 means that implant 1 can then easily be lifted out of the femur, for example by means of a hook in aperture 7 of end 6, with the minimum of damage.

I claim:

1. A hip implant for use in a resected femur which has a resected surface defined by a plane extending through the natural head/neck junction adjacent the articular cartilage, comprising an elongated stem having a single substantially linear axis defining a distal and a proximal portion, said stem having an exterior surface of a circular cross section throughout the length thereof; and said distal portion being smooth so as to avoid transmission of torsional forces to adjacent bony tissues when said stem is snugly received in a preformed aperture in said femur;

a flattened wedge-shaped portion of thickness less than that of the adjacent stem portion and having one end integral with said stem and extending medially a predetermined length from said proximal portion to an opposite end;

an articulating ball attached directly to said opposite end without interposition of any further elements and being shaped for rotary movement in a socket in an acetabulum, whereby, when said stem is implanted, said wedge-shaped portion is received in a corresponding preformed slot in a substantially intact bony neck of said femur, as defined by an area between a line through the trochanters and said plane along the head/neck junction of the femur such that said wedge-shaped portion is seated completely with in said slot and said predetermined length extends the entire distance through said area to allow for said ball to be seated substantially directly on said resected surface of the femur.

2. The hip implant of claim 1, wherein the stem is tapered along at least a part of said distal portion.

3. The hip implant of claim 1, wherein the end of the stem at said proximal portion extends beyond the wedge-shaped portion to a point level with the ball.

4. The hip implant of claim 3, wherein said distal portion is provided with means for receiving a hook whereby the implant may be removed.

5. The hip implant of claim 1, wherein the wedge-shaped portion is of flattened section throughout extending to said ball.

6. The hip implant of claim 1, wherein the wedge-shaped portion is textured, provided with indentations, or is both textured and provided with indentations, whereby bone interlock is encouraged.

7. The hip implant of claim 1 in combination with an end stop for receiving the distal portion.

8. A method of introducing to a human body a hip implant for use in a resected femur which has a resected surface defined by a plane extending through the natural head/neck junction adjacent the articular cartilage, and comprising an elongated stem having a single substantially linear axis defining a distal and a proximal portion of thickness less than that of the adjacent stem portion and, said stem having an exterior surface of a circular cross section throughout the length thereof; and said distal portion being smooth so as to avoid transmission of torsional forces to adjacent bony tissues when said stem is snugly received in a preformed aperture in said femur;

a flattened wedge-shaped portion having one end integral with said stem and extending medially a predetermined length from said proximal portion to an opposite end;

an articulating ball attached directly to said opposite end without interposition of any further elements and being shaped for rotary movement in a socket in an acetabulum, whereby, when said stem is implanted, said wedge-shaped portion is received in a corresponding preformed slot in a substantially intact bony neck of said femur, as defined by an area between a line through the trochanters and said plane along the head/neck junction of the femur such that said wedge-shaped portion is seated completely with in said slot and said predetermined length extends the entire distance through said area to allow for said ball to be seated substantially directly on said resected surface of the femur;

which method comprises:

removing only the ball from the body neck of the human femur;

reaming said preformed aperture in the femur of a size to snugly receive the stem of the implant;

providing said corresponding preformed slot in the body neck of said femur of a size to receive the wedge-shaped portion; and positioned said aperture and slot accurately in the femur to receive the implant whereby the ball projecting beyond the bony neck of the femur lies in the correct anatomical position.

* * * * *